United States Patent
Amthor et al.

(10) Patent No.: US 12,056,908 B2
(45) Date of Patent: Aug. 6, 2024

(54) MICROSCOPY SYSTEM, METHOD AND COMPUTER PROGRAM FOR PROCESSING MICROSCOPE IMAGES

(71) Applicant: Carl Zeiss Microscopy GmbH, Jena (DE)

(72) Inventors: Manuel Amthor, Jena (DE); Daniel Haase, Zöllnitz (DE); Thomas Ohrt, Golmsdorf (DE)

(73) Assignee: Carl Zeiss Microscopy GmbH, Jena (DE)

( * ) Notice: Subject to any disclaimer, the term of this patent is extended or adjusted under 35 U.S.C. 154(b) by 482 days.

(21) Appl. No.: 17/376,659

(22) Filed: Jul. 15, 2021

(65) Prior Publication Data
US 2022/0019828 A1 Jan. 20, 2022

(30) Foreign Application Priority Data

Jul. 17, 2020 (DE) ...................... 10 2020 119 042.5

(51) Int. Cl.
*G06V 10/22* (2022.01)
*G06N 3/08* (2023.01)
*G06T 7/00* (2017.01)
*G16H 30/40* (2018.01)

(52) U.S. Cl.
CPC ................ *G06V 10/22* (2022.01); *G06N 3/08* (2013.01); *G06T 7/0014* (2013.01); *G16H 30/40* (2018.01); *G06T 2207/10056* (2013.01)

(58) Field of Classification Search
CPC .......... G06V 10/22; G16H 30/40; G06N 3/08; G06T 7/0014; G06T 2207/10056
See application file for complete search history.

(56) References Cited

U.S. PATENT DOCUMENTS

| | | | | |
|---|---|---|---|---|
| 10,283,459 B2* | 5/2019 | Bhunia | ............. | H01L 23/53238 |
| 10,452,812 B2 | 10/2019 | Gogin et al. | | |
| 10,867,697 B2 | 12/2020 | Lyman et al. | | |
| 10,878,293 B2* | 12/2020 | Campanella | ......... | G06V 20/695 |
| 11,502,845 B2* | 11/2022 | Pope | ........................ | G06F 21/51 |
| 11,776,235 B2* | 10/2023 | Campanella | ............ | G06F 18/00 |
| 2011/0238768 A1 | 9/2011 | Habets et al. | | |
| 2019/0188830 A1 | 6/2019 | Edwards et al. | | |
| 2019/0197362 A1* | 6/2019 | Campanella | ......... | G06V 20/695 |
| 2022/0188393 A1* | 6/2022 | Forte | ..................... | H04L 9/3278 |

OTHER PUBLICATIONS

Dr. Leonhardt, Search Report for DE 102020119042.5, Jun. 14, 2021, 7 pages, no English translation.
Majtner, Tomas et al., "Comparison of Deep Learning-Based Recognition Techniques for Medical and Biomedical Images," University of Southern Denmark, 2019, 13 pages.
Shin, Hoo-Chang et al., "Medical Image Synthesis for Data Augmentation and Anonymization using Generative Adversarial Networks," NVIDIA Corporation, Sep. 13, 2018, 11 pages.

* cited by examiner

*Primary Examiner* — Hosuk Song
(74) *Attorney, Agent, or Firm* — LaBatt, LLC

(57) ABSTRACT

A method for processing microscope images comprises: acquiring a microscope image captured by a microscope; identifying at least one image section with sensitive information within the microscope image by means of an image processing program which uses provided reference information regarding sensitive information; rendering unrecognizable the at least one identified image section with sensitive information in order to generate an anonymized image; and outputting the anonymized image.

23 Claims, 6 Drawing Sheets

MICROSCOPY SYSTEM, METHOD AND COMPUTER PROGRAM FOR PROCESSING MICROSCOPE IMAGES

REFERENCE TO RELATED APPLICATIONS

The current application claims the benefit of German Patent Application No. 10 2020 119 042.5, filed on 17 Jul. 2020, which is hereby incorporated by reference.

FIELD OF THE DISCLOSURE

The present disclosure relates to a microscopy system as well as to a method and a computer program for processing microscope images.

BACKGROUND OF THE DISCLOSURE

Digital image processing is playing an increasingly important role in modern microscopes. In particular machine learning programs are being exploited more intensively for numerous applications. For example, methods based on machine learning programs have been developed by the Applicant to perform an autofocusing, an automatic sample container identification, e.g. for documentation purposes or for navigation, a determination of the dimensions of or a distance to sample containers, or a stitching of a plurality of captured images. The quality of these steps depends, among other things, on the training data available to the machine learning program. It is thus desirable that the microscope images used in the training cover a wide spectrum of possible areas of application. A sharing, disclosure or dissemination of microscope images from different sources is, however, often not possible, for example in the medical sector when microscope images contain patient-related information, or in the field of research and development where the microscope images indicate research results that are not intended to be disclosed to third parties. For modern machine learning programs for processing microscope images, the availability of comprehensive training data thus poses a challenge.

The present disclosure is, however, not restricted to the areas just mentioned for the purposes of illustration; rather, it relates generally to the image processing of microscope images containing sensitive information, said image processing not necessarily involving a use of machine learning applications.

SUMMARY

It can be considered an object of the invention to provide a method, a computer program and a microscopy system which make microscope images with sensitive information more generally exploitable in an efficient manner by means of image processing.

This object is achieved by means of the method with the features of claim 1, by means of the computer program of claim 22 and by means of the microscopy system with the features of claim 23.

A method for processing microscope images according to the invention comprises receiving a microscope image captured by a microscope. At least one image section with sensitive information is identified within the microscope image by means of an image processing program which uses provided reference information regarding sensitive information. The at least one identified image section with sensitive information is then rendered unrecognizable or unidentifiable in order to generate an anonymized image. The anonymized image is then output.

A computer program according to the invention comprises commands that cause the execution of the method according to the invention when the computer program is executed by computer.

A microscopy system according to the invention comprises at least one microscope for capturing a microscope image and at least one computing device. The computing device is configured to identify at least one image section with sensitive information within the microscope image by means of an image processing program which uses provided reference information regarding sensitive information. The computing device is further configured to render the at least one identified image section with sensitive information unrecognizable in order to generate an anonymized image and to output the anonymized image.

As the image processing program is designed to automatically localize image areas with sensitive information and subsequently remove this information from the microscope image, it is possible to generate anonymized images in which the remaining image content, with the exception of the sensitive information, is essentially preserved. The remaining image content can be exploited for further processing/evaluation steps.

To use a potential example for the purposes of illustration, the microscope image can be captured by an overview camera and contain a sample carrier with a plurality of sample chambers as well as an adhesive label that includes written details regarding the samples. It is intended that such an overview image should become part of training data of a machine learning application by means of which the sample chambers in the overview image are localized automatically. The adhesive label is not necessary for the purposes of the machine learning application, yet the written details it displays regarding the sample prevent the captured image from being sharable, for example with the developer of the machine learning application. This is remedied by localizing the image area of the adhesive label with the written details and rendering this image area unrecognizable, for example by replacing the text on the label with blank areas from the same (inpainting). The removal of this sensitive information allows an unhindered exploitation of the remaining image content of the microscope image.

Optional Embodiments

Advantageous variants of the microscopy system according to the invention and of the method according to the invention are the object of the dependent claims and are explained in the following description.

The microscope image can be an overview image or a sample image of a microscopic sample. An overview image shows at least a part of a sample carrier, for example at least an edge of a sample chamber. It can be captured in particular with an overview camera, which can be provided in addition to the microscope camera. The overview camera optionally views a sample carrier or sample stage obliquely, i.e. at an angle in relation to the optical axis, which can correspond to the longitudinal axis of a currently active microscope objective. Alternatively, an overview image can also be captured via a microscope objective and the microscope camera, wherein it then differs from a sample image in that a microscope objective with a lower magnification is used for its capture. It is possible with some measurements that only a sample carrier is visible in an overview image and not the sample itself.

Identifying an Image Section with Sensitive Information

What is considered sensitive information can vary depending on the use case. The image processing program comprises reference information by means of which it is possible to find certain objects or image areas in a microscope image. The reference information thus determines which image sections can be identified and the objects and image areas that can be localized by means of the provided reference information of the image processing program can be defined as sensitive information.

The predetermined reference information can relate in particular to one or more of the following: a cover slip area (cover glass area) of a sample carrier; one or more sample chamber areas; one or more sample areas on a sample carrier and/or a background area outside a sample carrier. These types of sensitive information can occur in particular in an overview image of a microscope. In these cases, the image processing program can localize where an image section constituting or comprising a cover slip area, a sample chamber area, a sample area on a sample carrier or a background area outside a sample carrier is located in the microscope image. Reference information relating to different types of sample chamber areas can be provided, for example relating to rectangular and to circular sample chambers and/or relating to wells of different sizes of different types of microtiter plates. A background area can show, for example, microscope components or a laboratory environment that a microscope user may not wish to show so that background areas can generally be treated as sensitive information.

The reference information can additionally or alternatively relate to text, adhesive labels or markings on sample carriers. It is thereby possible to identify in the microscope image one or more image sections in which the sensitive information is text, an adhesive label or a marking on the sample carrier. The reference information can specify that not every type of text is to be evaluated as sensitive information. For example, letters and numbers which form part of a sample carrier and which per se do not constitute a description of the collected samples or of the conducted experiment, e.g. as is the case with the column and row numbers of a microtiter plate or a designation of a manufacturer of a sample carrier, can be assessed as non-sensitive text. The text classified as sensitive information can be handwritten or typewritten and differ in size, color and font. Reference information can be provided in order to always identify handwritten text as sensitive information.

Alternatively or additionally, the predetermined reference information regarding sensitive information can also relate to one or more sample types, in particular biological cells, cell organelles, tissue sections or pathology data. With this reference information, the image processing program can thus localize an image section containing, for example, these specific cell organelles, pathological image areas potentially indicating a specific patient, or patient-relevant information (in text form). If the object to be analyzed/sample is an electronic component, the reference information can also relate to a product ID or a designation of the manufacturer of the component.

A shape can be predetermined for the at least one image section with sensitive information, i.e. in particular without regard to the current microscope image. The shape of the image section is thereby disassociated or rendered independent from a shape associated with the sensitive information. For example, a rectangle or a circle can be predetermined as shape for the image section, while the sensitive information relates to a biological cell type so that the shape associated with the sensitive information is accordingly the shape of this biological cell. In other words, the image section that is rendered unrecognizable can always include an area surrounding the sensitive information in order to disguise the shape that relates to the sensitive information.

The image processing program can be designed to provide a user with a selection of options regarding the type of sensitive information for which corresponding image sections are to be rendered unrecognizable. The image processing program can use reference information relating to different types of sensitive information in this case. The process of identifying and rendering an image section unrecognizable then only concerns image sections that relate to the types of sensitive information selected by the user. For example, the user can choose whether sample areas and/or text and/or a background are to be treated as sensitive information.

Alternatively to a manual selection, the image processing program can also be designed to automatically select the types of sensitive information for which corresponding image sections are rendered unrecognizable. The selection in this case occurs based on an image content of the microscope image or a contextual datum relating to the microscope image. The image processing program can in particular perform the selection of the types of sensitive information depending on one or more of the following factors:

The selection can occur as a function of whether the microscope image is an overview image or a sample image. For example, text and/or background areas, which typically do not occur in sample images, can be sensitive information for an overview image. On the other hand, certain cells that can be classified as sensitive information are generally only found in sample images and not in overview images.

The selection can also occur as a function of parameters and settings on a microscope stand or of a microscope component, for example as a function of a light setting, a filter setting, a camera setting or a setting relating to a microscopy method such as, e.g., phase-contrast or fluorescence microscopy. Such settings can permit an inference regarding the type of experiment and thus regarding a type of sensitive information specific to a sample type.

The selection can also occur as a function of a file name of the microscope image or of a detail linked to a file of the microscope image. Such a detail can relate to, for example, file metadata, a date of capture, a file creator, a folder name and/or an image resolution.

The selection can also occur as a function of a sample type or sample carrier type used during the capture of the microscope image. For example, reference information regarding a position of text fields/descriptive fields deemed sensitive information can be linked to the sample carrier type.

The selection can further occur as a function of a text content on a sample carrier. For example, it can be provided that text that is not specific to an experiment is not anonymized, in particular manufacturer/model names or column and row numbers of a multi-titer plate, while other details, in particular regarding the analyzed sample, are rendered unrecognizable.

Identifying an Image Section by Means of a Machine Learning Algorithm

The image processing program can comprise a trained reference model of a machine learning algorithm/machine learning model that performs the identification of at least one image section with sensitive information. The reference information regarding sensitive information is provided in the form of model parameters, in particular model weights, in the trained reference model. The reference model can be, for example, a convolutional neural network (CNN), which has a number of parameters that are defined in a training process. These parameters can be weights or model weights.

The image processing program or reference model can be designed to identify an image section with sensitive information by means of segmentation or detection. In the case of a segmentation, the microscope image is divided into different areas, i.e. each image pixel is allocated to a unit. The image processing program can be designed in particular to recognize different objects, wherein some of these objects count as sensitive information while others do not. For example, the segmentation can identify the edges of a sample carrier and sample chambers located within said edges, wherein the sample carrier area (surrounding the sample chambers) is not treated as sensitive information while the sample chambers that contain samples to be analyzed are treated as image sections with sensitive information.

The image processing program or reference model can also be designed to perform a classification of the microscope image by means of which the microscope image is assigned to one of a plurality of possible image classes. A position of at least one image section with sensitive information is respectively stored as reference information for different image classes. The identification of an image section with sensitive information then occurs by using the stored position for the determined image class. For example, a classification of the microscope image can reveal the type of sample carrier used. The location of descriptive fields where individual details, i.e. sensitive information, are entered is known for different sample carriers. As the position of these descriptive fields in the microscope image or the position of these descriptive fields in relation to the position of the sample carrier in the microscope image is known, the corresponding area in the microscope image can be evaluated as an image section with sensitive information. An image section is thus not necessarily evaluated as an image section with sensitive information based on its content, but rather on the basis of its position by taking into account the reference information stored for the determined image class. These steps can be implemented by means of a machine learning algorithm or by means of a classic image processing program without a machine learning algorithm.

The method of the invention can also optionally comprise a training of the reference model of the machine learning algorithm in order to define the model parameters. The training can be conducted in particular with pairs each consisting of a training image and an associated target image, wherein training images contain image sections with sensitive information and areas corresponding to these image sections in terms of their position are tagged or modified, in particular rendered unrecognizable, in the associated target images. Such a training makes it possible, for example, to classify text either as sensitive information or as non-sensitive information with precision based on its content and based on its position in relation to the sample carrier.

The reference model of the machine learning algorithm can also be designed to perform the operation of rendering identified image sections unrecognizable. The microscope image can be the input for the reference model in this case while its output is an anonymized image. For example, the image processing program can comprise a neural network trained by means of a machine learning algorithm, in particular a convolutional neural network, CNN, or a generative adversarial network, GAN, which generates the anonymized image directly from the microscope image. To this end, the neural network can be trained with pairs each consisting of a training image and an associated target image, wherein training images contain image sections with sensitive information and areas corresponding to these image sections in terms of their position are rendered unrecognizable in the associated target images.

Optionally, the image processing program can comprise an autoencoder trained by means of a machine learning algorithm, which generates the anonymized image directly from the microscope image. To this end, the autoencoder is trained with training images that do not contain any image sections with sensitive information. An autoencoder can generally be understood as a pair of functions consisting of an encoder and a decoder, wherein the encoder generates a low-dimensional encoding from an input image and the decoder in turn generates an output image from the output of the encoder. The encoder and decoder are trained in such a manner that an error (a deviation) of the output image in relation to the input image is minimized. An autoencoder thus generates an output image that generally closely resembles the input image. This process is used, for example, for data compression or for the purposes of a simple visualization. As the training data only contains microscope images without sensitive information in this case, the autoencoder is trained to be able to reproduce only those input images that do not contain any sensitive information with precision. If an input image deviates significantly from the training data, then the autoencoder is unable to reproduce this deviation or is only able to reproduce this deviation poorly so that, as a consequence, this deviating content is missing in the output image of the autoencoder or is distorted in the output image. As the training data does not contain any image sections with sensitive information, the autoencoder is unable to replicate this information in the output image. The removal of sensitive information by an autoencoder can be considered an identification and rendering unrecognizable of image sections with sensitive information in the sense of this disclosure.

Rendering the Identified Image Section Unrecognizable

Rendering the identified image section with sensitive information unrecognizable is intended to be understood in the sense that the content of the image section is modified in such a manner that the sensitive information is no longer recognizable or is completely removed. Either the entire image section, for example a rectangle, can be rendered unrecognizable or solely a part that contains the sensitive information in this image section, for example the image pixels that represent the letters of a piece of sensitive information. Rendering unrecognizable (obfuscation) can occur, for example, by pixelating, adding noise to, smoothing or blurring the identified image section. Pixelating is understood to mean that a plurality of adjacent image pixels are assigned the same value so that the image information is partially lost. Noise addition denotes a random modification of the pixel values in the image section, whereby the original pixel values can no longer be reconstructed. Blurring, for example by means of a Gaussian filter, denotes an averaging or blending of a plurality of adjacent image pixels. It is also possible to use other image filters which modify the image content to such an extent that the original content is no longer recognizable or reconstructable, for example by means of an averaging of the image pixels.

Alternatively, rendering an identified image section with sensitive information unrecognizable can also occur by replacing the identified image section or parts of the same using image content from the surrounding area. For example, image pixels of a text can be replaced with adjacent pixel values or filled as a function of the adjacent pixel values representing, for example, a descriptive field or a background. Such a filling allows a color or intensity gradient of adjacent image areas to be continued in the image section that is to be rendered unrecognizable. This makes it possible to generate a particularly natural image impression.

If the sensitive information in question is a text, then rendering it unrecognizable can also occur by replacing the text with another, in particular meaningless, text. The new text can conform to the original text in terms of size and font.

The operation of rendering an identified image section unrecognizable can also occur by means of a machine learning program. The identified image section can thus be fed to a neural network trained to fill an image region based on contextual data from adjacent regions. An output of the neural network then replaces or manipulates the identified image section. This type of process is also called inpainting. The neural network can in particular be designed as an image-to-image CNN or GAN.

The operation of rendering an identified image section unrecognizable can alternatively occur by means of an autoencoder. The identified image section is fed to the autoencoder, which generates an output therefrom that replaces the identified image section. The autoencoder is trained with training images that do not contain any sensitive information. Analogously to the described variant in which an autoencoder is used both for identifying and rendering unrecognizable an image section with sensitive information, the selection of training data determines which information the autoencoder can reproduce and which information is missing in the output of the autoencoder. An autoencoder can be rendered suitable, for example, for rendering specific samples unrecognizable through the use of training data in which such samples do not occur.

A particularly reliable way of rendering an identified image section unrecognizable can alternatively be achieved by excising or truncating the identified image section. Image information is thus no longer provided for the image section in question. The identified image section can also be replaced by a predetermined content (i.e. by a substitute content independent of the microscope image), for example by a predetermined pattern or a predetermined color.

A further option for rendering an identified image section unrecognizable consists in the deletion of a certain color channel of the microscope image. A microscope image can comprise a plurality of color channels, wherein each image pixel comprises a respective value per color channel. Single color channels often depict specific cell structures so that, simply by removing a certain color channel, information regarding these cell structures is essentially removed from the microscope image while the information of other color channels is preserved. The deletion of a color channel can mean in particular that its values are set to a constant, e.g., zero. The deletion can occur in the identified image section only, whereby the image quality outside the identified image area is not impaired, or alternatively for the entire microscope image, which prevents a potential inference of the sample or sample characteristics from the color channel used.

The image processing program can optionally provide a user with a selection of options regarding the manner in which identified image sections are rendered unrecognizable. In this case, the image processing program is capable of rendering an image section unrecognizable in different ways. For example, it is possible for an inpainting to occur by default, i.e. the image pixels of the sensitive information are replaced by means of the pixels of the surrounding area for a realistic image impression. However, should a user be of the opinion that the sensitive information has not been or is not being rendered unrecognizable to a sufficient degree, then the user can opt, for example, to replace the entire identified image section with a predetermined pattern.

Optionally, the image processing program can be designed to perform a type of obfuscation (i.e., the operation for rendering an identified image section unrecognizable) dependent of the sensitive information. In this case, it is possible to select different methods for rendering an image section unrecognizable from those mentioned, in particular as a function of the type of information detected. If the sensitive information contained in an image section is text, then rendering said image section or a part of said image section unrecognizable can occur, for example, by means of a replacement with image content from a surrounding area, while, if the sensitive information contained in an image section is not text, then rendering said image section or a part of said image section unrecognizable occurs in a manner other than by means of a replacement with image content from a surrounding area, e.g., by pixelation or replacement with a predetermined content.

Exploiting Anonymized Images

The invention also relates to a method for utilizing microscope images, wherein at least one computing device executes the described method for processing a microscope image and thus generates at least one anonymized image. The at least one computing device transmits the anonymized image to a central computing device that does not have access to the captured microscope image. It is thus essentially possible for the central computing device to receive and use the information content of the microscope image with the exception of the sensitive information.

The terms "computing device" and "central computing device" are used for the purpose of differentiation and both can in principle be or comprise any computer, server or cloud-based system. The computing device can in particular be connected to a microscope or be allocated to a certain microscope and also serve to control the microscope. For example, the computing device can comprise a personal computer or one or more processors, in particular as part of a microscope. Alternatively, the computing device can be formed by servers or cloud-based systems. A local or technical connection to a microscope is not necessarily required, as it is sufficient when the computing device can load a microscope image from a data memory.

The central computing device can comprise any computer, server or cloud-based computing system and be spatially separate from the microscope and from the computing device. The central computing device can communicate with the computing device, for example, via the internet or another network. Alternatively, a data transfer between the two can occur in isolation, without a permanent communications link. Again, the terms "central computing device" and "computing device" are used for the purpose of a better differentiation, there not necessarily being a difference with respect to their physical design.

The at least one computing device can be configured to display the anonymized image to a user for release approval and to transmit the anonymized image to the central computing device only after release approval has been given. The user can thereby verify that the sensitive information has really been removed. The computing device can provide the user with an input tool with which further image sections can be manually tagged in order to undergo further operations to render them unrecognizable. The information regarding which image sections were manually tagged can also be transmitted and exploited for the improvement of the image processing program so that the image processing program is ideally eventually able to automatically detect all image sections with sensitive information with no exceptions.

It is particularly advantageous when a plurality of computing devices respectively execute the described method for processing a microscope image and thereby respectively generate at least one anonymized image before transmitting the generated anonymized image to the central computing device. The central computing device, on the other hand, does not have access to the captured microscope images and instead uses the anonymized images for a joint data evaluation. The central computing device can thus use the anonymized images (in particular in a processed form) as or for training images of a machine learning application. This makes it possible to improve the aforementioned examples of machine learning algorithms or to train other machine learning algorithms that are not used to anonymize microscope images.

General Features

A microscope here can be understood to be in particular an optical microscope or a measurement device of some other design that is configured to capture images (microscope images). Depending on the variant embodiment of the invention, the image acquisition process can form part of the method or the method can begin with the loading of microscope images already provided.

A sample carrier can be understood to be any support in or on which a sample is intended to be received. In particular, a sample carrier can be or comprise a slide made of, for example, glass, a multi-well or microtiter plate, a Petri dish, a capillary or a counting chamber. The sample carrier can comprise a plurality of sample chambers, which are understood to be areas separated from one another laterally for receiving a plurality of samples.

An anonymized image is understood as an image derived from a microscope image in which the sensitive information contained in the microscope image has been removed or rendered unrecognizable. An image section containing, in addition to the sensitive information, an area surrounding the sensitive information may be rendered unrecognizable or only the part of the image section that displays the sensitive information. Depending on the embodiment, a remaining image area outside the image section can remain unaltered or be modified. The latter is the case, for example, when a color channel is removed for the entire microscope image or when an autoencoder or GAN is used to calculate areas of the anonymized image from areas of the microscope image.

Wherever described method steps imply a sequence here, it is also possible to insert further processes into said sequence. In particular, data processing and data modifications can be carried out. For example, the microscope image does not have to be a raw image captured by a microscope, but rather one or more such raw images can have been processed beforehand in order to create the microscope image.

The computer program of the invention can comprise in particular the described variants of the image processing program for generating the anonymized image. The computer program can also comprise commands by means of which the function of the central computing device and the communication with the computing devices are realized. The computer program can be formed by independently operable software packages, wherein the packages are intended to be run on different computers, for example on the computing devices and the central computing device.

The characteristics of the invention that have been described as additional microscope features also yield, when implemented as intended, variants of the method according to the invention. Conversely, the microscopy system can also be configured to carry out the described method variants.

BRIEF DESCRIPTION OF THE DRAWINGS

A better understanding of the invention and various other features and advantages of the present invention will become readily apparent by the following description in connection with the schematic drawings, which are shown by way of example only, and not limitation, wherein like reference numerals may refer to alike or substantially alike components.

DETAILED DESCRIPTION OF EMBODIMENTS

Different example embodiments are described in the following with reference to the figures.

FIGS. 1 to 4

Figure 1:
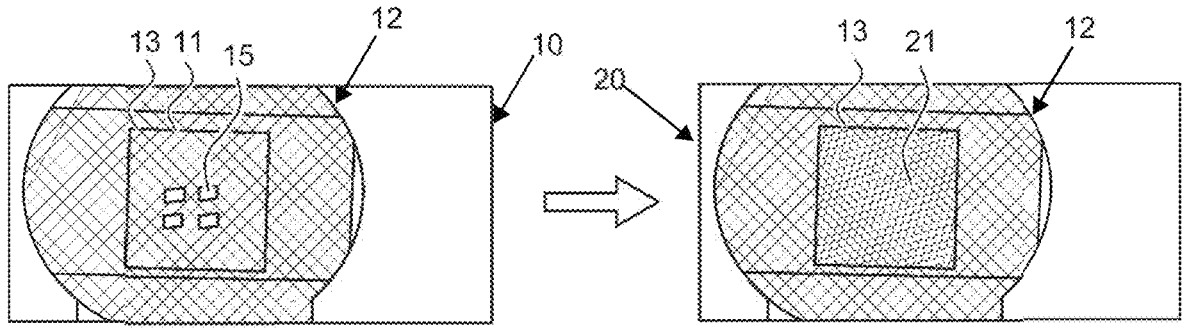
FIG. 1 shows schematically a microscope image with sensitive information and an anonymized image calculated therefrom according to the invention.
Figure 2:
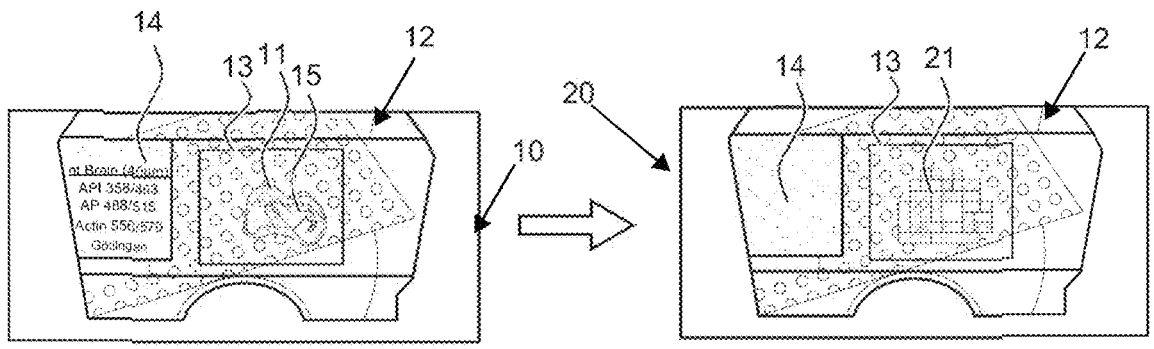
FIG. 2 shows schematically a further microscope image with sensitive information and an anonymized image calculated therefrom according to the invention.
Figure 3:
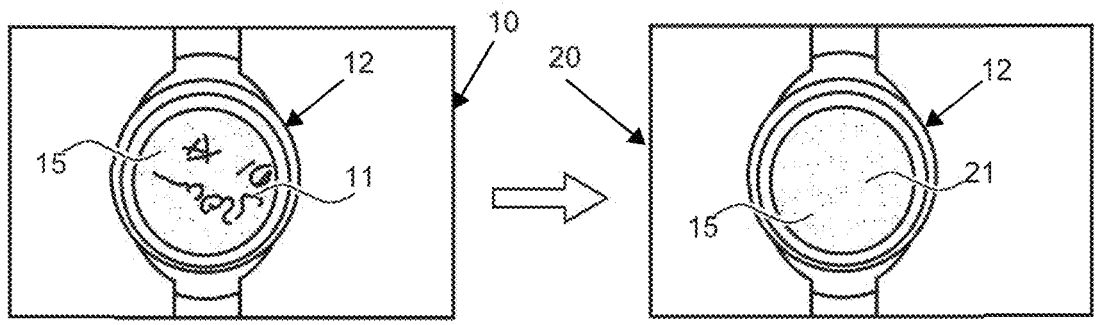
FIG. 3 shows schematically a further microscope image with sensitive information and an anonymized image calculated therefrom according to the invention.
Figure 4:
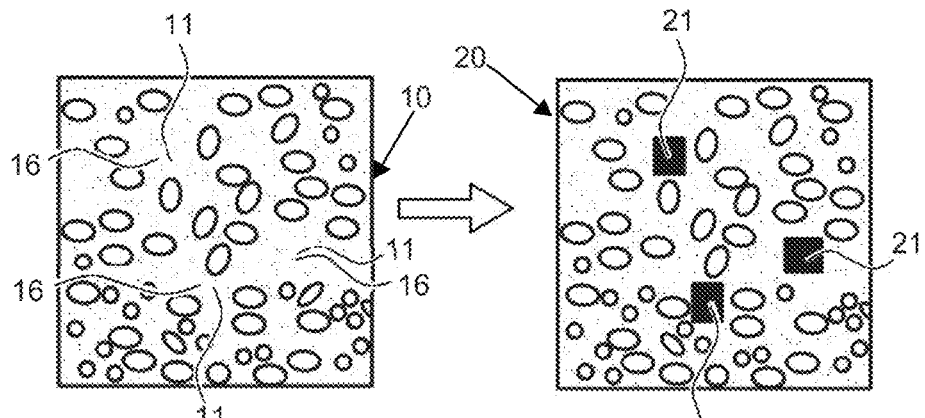
FIG. 4 shows schematically a further microscope image with sensitive information and an anonymized image calculated therefrom according to the invention.

FIGS. 1 to 4 respectively show schematic illustrations of a microscope image 10 captured by a microscope. In FIGS. 1 to 3, the illustrated image is an overview image showing a sample carrier 12. A sample 15 supported by the sample carrier 12 is recognizable in the overview image in different measurement situations. FIG. 4, on the other hand, shows a sample image captured using a higher magnification. Structures of the actual sample are recognizable in the sample image, in this case different biological cells.

It would be useful be able to share the microscope images 10 for different practical applications such as, for example, technical support or the improvement of machine learning applications. Technical support provided to a microscope user is often much more efficient when a microscope image 10 captured by that user is available. With regard to machine learning applications, training data that covers the real measurement situations to the greatest extent possible should ideally be available; it is thus advantageous if the microscope images 10 captured by a microscope user can be used for the training data. This is, however, frequently not possible, as the captured microscope images 10 can contain sensitive information that the microscope user is not permitted or does not wish to share. Sensitive or critical information can be, for example, descriptive text, sample areas in overview images or specific sample structures in sample images.

The microscope image 10 in FIG. 1 shows a sample carrier 12 with a cover slip 13, under which a sample 15 is located. The image areas of the sample 15 are classified here as sensitive information that is not to be shared.

Similarly, the microscope image 10 of FIG. 2 shows image areas of a sample 15 which are classified as sensitive information and are not to be shared. In addition, this microscope image 10 contains a descriptive field 14 with, among other things, details regarding the sample 15. Any text content of the descriptive field 14 is also classified as sensitive information that the microscope user is not permitted to disclose to or share with third parties.

The microscope image 10 shown in FIG. 3 depicts a sample carrier 12 on the cover slip of which a handwritten note has been made that is classified as sensitive information and is not to be shared. Particular details of the sample 15 are not discernible in this case so that it is not necessary to treat such as sensitive information.

The microscope image 10 of FIG. 4 shows a part of the sample, here a plurality of cells which include cells or sample structures 16 specific to the experiment in question. The specific sample structures 16 represent sensitive information for the microscope user, while other areas of the sample do not contain any information requiring protection.

By means of example embodiments of the invention, an anonymized image 20 is respectively calculated from the microscope images 10. An image section 11 of the microscope image 10 with sensitive information is replaced in the anonymized image 20 with an area 21 that has been rendered unrecognizable. The anonymized image 20 thus essentially corresponds to the microscope image 10 with the difference that the sensitive information has been removed. In the example shown in FIG. 1, the cover slip area 13 is localized in the microscope image 10 and this area is replaced in the anonymized image 20 by a pattern. In the example shown in FIG. 2, the image section 11 with the sample 15 is pixelated and thus unrecognizable. The descriptive field 14 is also identified as such and any text located therein excised. FIG. 3 illustrates the filling of image pixels of a text (script) with image pixels from a surrounding area, which produces a natural image impression. In the case of FIG. 4, the image areas of the specific sample structures 16 are modified, i.e. blacked out, so as to become unrecognizable areas 21. The anonymized images 20 can now be shared, for example, with a technical client support, a provider of image processing tools or a developer of machine learning applications. Further examples of possible fields of application are the storage of image data at sites classified as unsafe, for example external servers, or the use of cloud-based image evaluation services of third-party suppliers.

Figure 5:
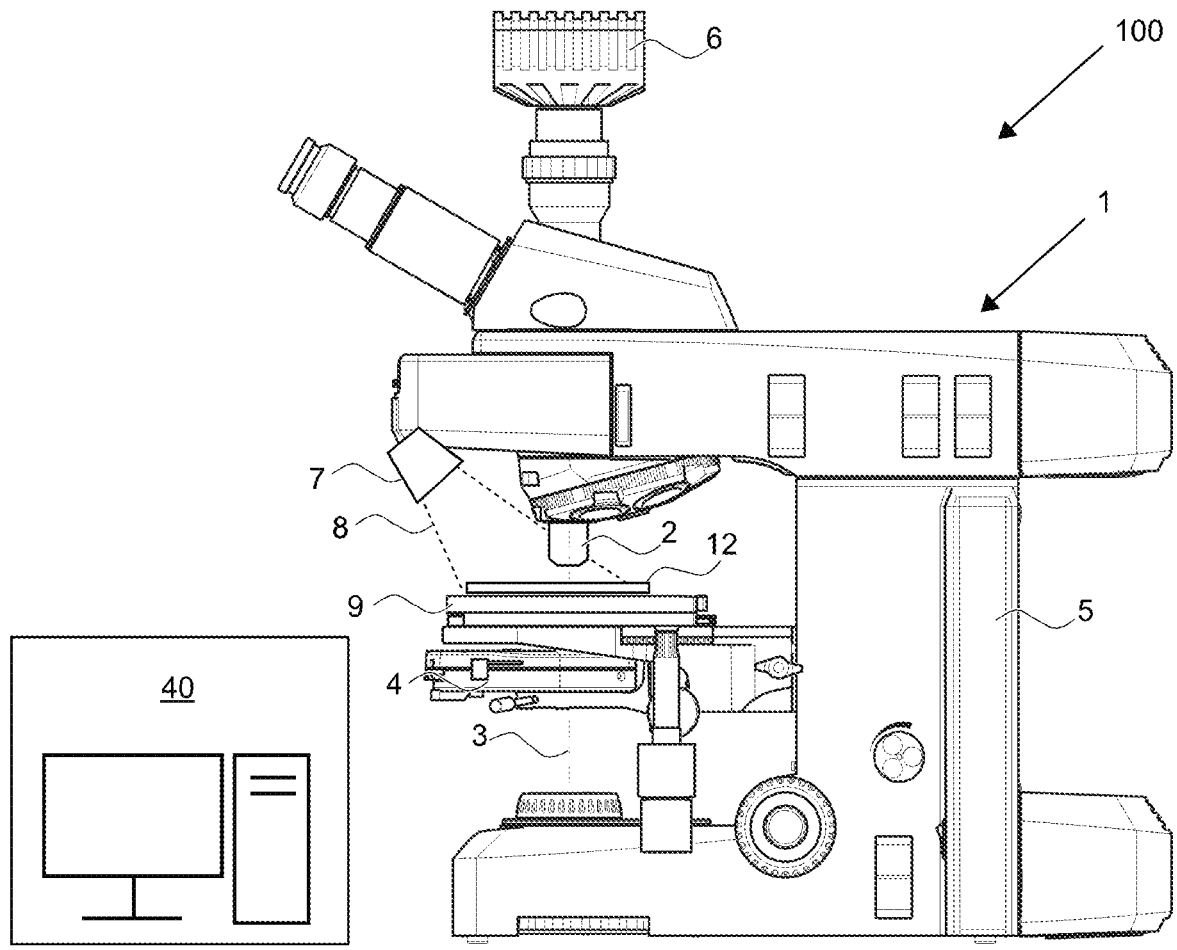
FIG. 5 shows schematically an example embodiment of a microscopy system of the invention.

Example Embodiment of FIG. 5

An example embodiment of a microscopy system 100 according to the invention is shown schematically in FIG. 5. The microscopy system 100 comprises a microscope 1 with a microscope stand 5, at least one microscope objective 2, a microscope camera 6, which receives detection light guided via the microscope objective 2, a light source for illuminating a sample and a condenser 4 for guiding light of the light source to the sample. The microscope 1 further comprises a sample stage 9 by means of which a sample carrier 12 can be supported. An optical axis 3 of the microscope objective 2 is often perpendicular to the sample stage 9 or a surface of the sample carrier 12.

In the shown example, the microscope 1 comprises at least one additional overview camera 7, the field of view 8 of which is illustrated by means of dashed lines. The overview camera 7 is aimed at the sample carrier 12 in order to capture a (macroscopic) overview image of the sample carrier 12. A larger portion of the sample carrier 12 is thus visible in the overview image than is the case with a sample image captured via the microscope objective 2 and the microscope camera 6 arranged behind it. In a variant of the illustrated embodiment, the overview camera 7 does not view the sample carrier 12 directly, but rather via a deflection mirror. The deflection mirror can be arranged, for example, on the objective revolver and be selected instead of the microscope objective 2.

It is also possible to provide an inverted microscope arrangement instead of the illustrated upright arrangement. The positioning of the overview camera 7 can also vary. Moreover, it can also be provided that, instead of using a separate overview camera 7, the microscope camera 6 captures overview images by switching to a microscope objective with a lower magnification.

The microscope images described here can be overview images or sample images. They are fed to a computing device 40, which is configured to generate the anonymized images shown in FIG. 1. The computing device 40 can be designed as part of the microscope 1 or as a supplementary unit, wherein the microscope 1 and the computing device 40 together form the microscopy system 100. The computing device can also be formed by electronics arranged on the microscope 1 or in the microscope stand 5. Alternatively, the computing device 40 can be a computer arranged next to the microscope 1 or at a distance from the microscope 1 and receive microscope images from the microscope 1 or a data memory connected to the same via a communications link.

The computing device 40 can be configured to execute the example embodiments of the method according to the invention, which are described with reference to the following figures.

Figure 6:
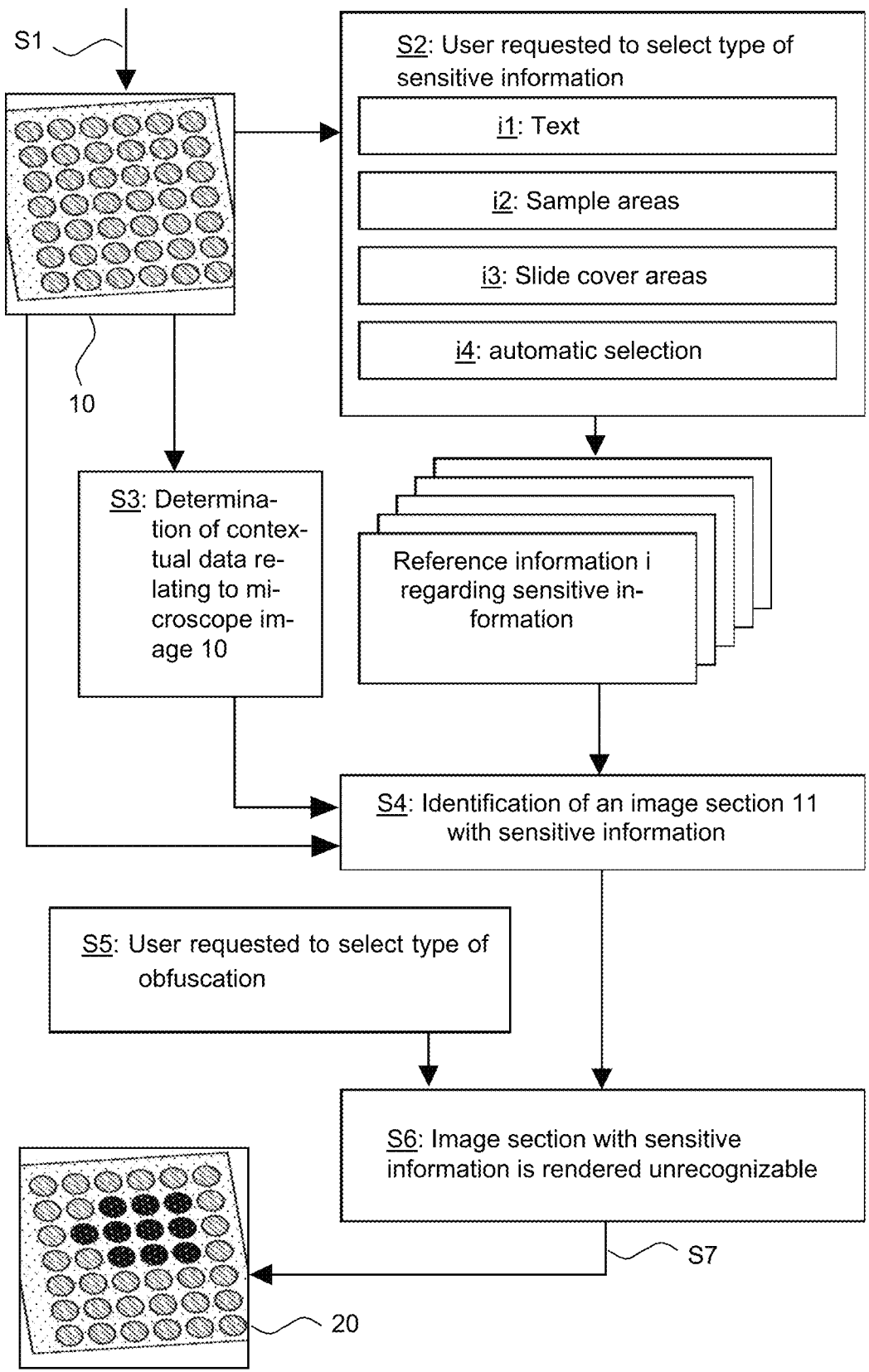
FIG. 6 illustrates schematically process steps of an example embodiment of a method of the invention.

Example Embodiment of FIG. 6

An example embodiment of a method according to the invention for processing microscope images 10 is illustrated schematically in FIG. 6. A computer program according to the invention is designed to execute this method.

First, at least one microscope image 10 is acquired in step S1, for example loaded from a memory or received from a microscope. In an optional step S2, a user is presented with different options i1-i4 concerning relevant types of sensitive information. This allows the user to choose which information is classified as sensitive and is to be removed from a microscope image. For example, the user can indicate text i1, sample areas i2 or cover slip areas i3 as sensitive information. Alternatively, a user can opt for an automatic selection i4 as a setting.

As a function of the selection made in step S2, corresponding predetermined reference information i regarding different types of sensitive information is used. The reference information i is stored in a memory or as data of an image processing program. The reference information i can comprise information for detecting the respective structures in an image, for example information for the purpose of detecting text. Additionally or alternatively, the reference information can also comprise locational information indicating the position of the sensitive information in relation to the sample carrier. For example, locational information can indicate where a descriptive field is located on a sample carrier. Locational information provided as reference information i can also be direct coordinates of the microscope image 10 and thus define an image section in the microscope image 10.

By means of the reference information i, at least one image section 11 with sensitive information is localized in the microscope image 10 in step S4. For example, a segmentation of the microscope image 10 can occur via image processing in order to divide the image into different areas such as "cover slip area", "sample carrier area outside the cover slip" and "background outside the sample carrier". If the type of sample carrier in question is determined, reference information stored for this sample carrier concerning the location of a descriptive field can be utilized. This information is used to localize the image area of the descriptive field in the microscope image. Alternatively, it is possible, for example, for all cover slip areas or all sample chambers containing samples to be detected as image sections with sensitive information.

Optionally, contextual data determined for the microscope image in a previous step S3 can also be taken into account in step S4. The contextual data can be, for example, information relating to the file of the microscope image, for example a file or folder name, or information regarding the measurement, for example microscope settings. For example, a series of measurements performed with the same sample carriers and/or similar cover slips can be inferred from this information. It is also possible to infer from the contextual data whether the microscope image is a sample image or an overview image. Certain types of sensitive information, in particular cover slip areas, adhesive labels or text, are optionally only sought in overview images and not in sample images. A user/company name linked to certain sensitive information to be rendered unrecognizable can also function as a contextual datum, for example it can be stipulated that cover slip areas are always to be rendered unrecognizable for a certain user.

After the image sections 11 with sensitive information have been localized in step S4, they are rendered unrecognizable in step S6, for example blacked out or replaced by a predetermined pattern. An anonymized image 20 is thus generated, which is finally output in step S7.

It is optionally possible to add a step S5 in which a user is presented with a selection of obfuscation options, i.e., options concerning how sensitive information is to be rendered unrecognizable. The possible options can be, for example, blacking out, pixelating, blurring, filling with content from a surrounding area or replacing text with meaningless text. In principle, step S5 can occur at any point prior to the execution of step S6.

Figure 7:
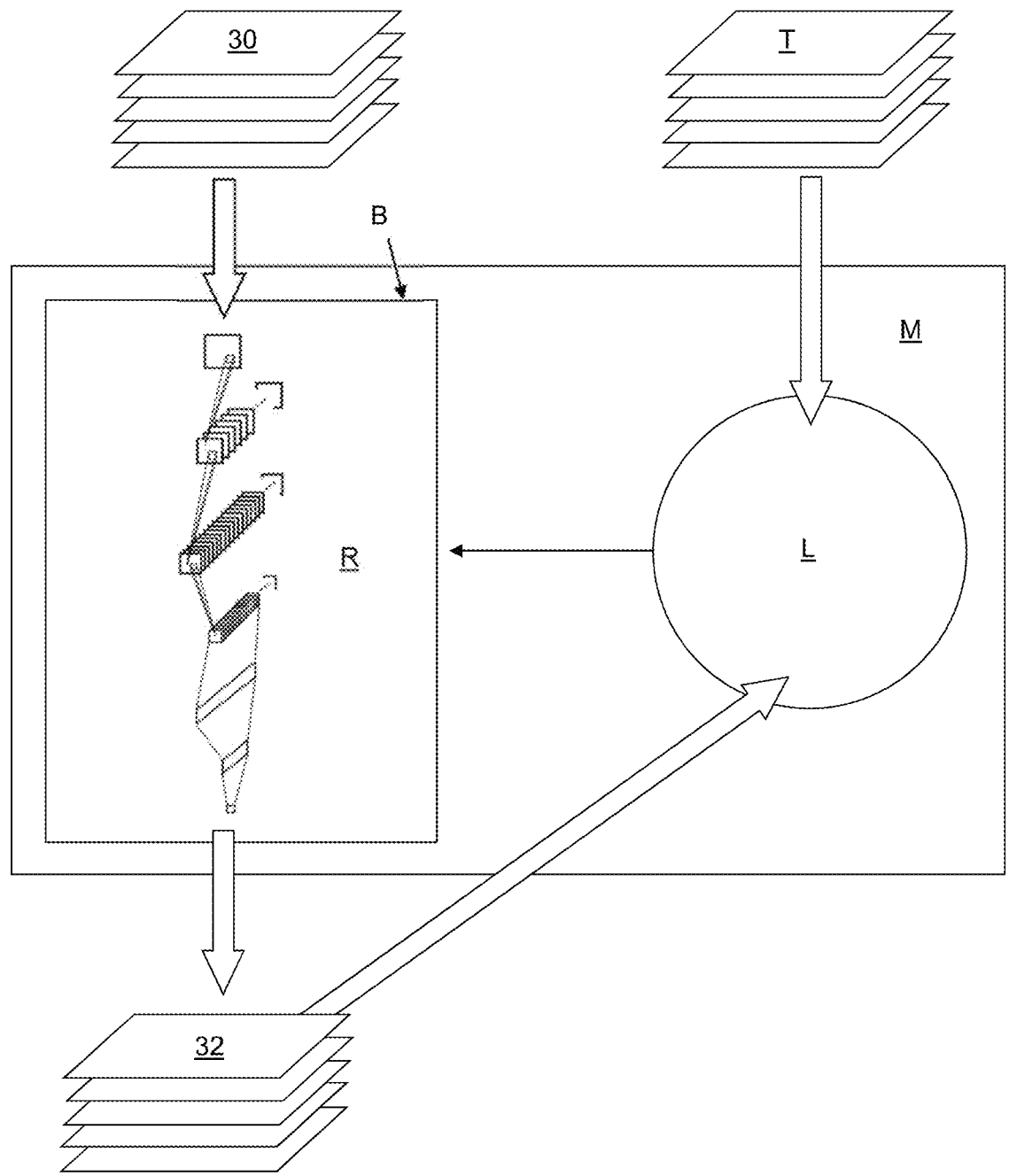
FIG. 7 illustrates schematically process steps of a machine learning algorithm of example embodiments of the method of the invention.
Figure 8:
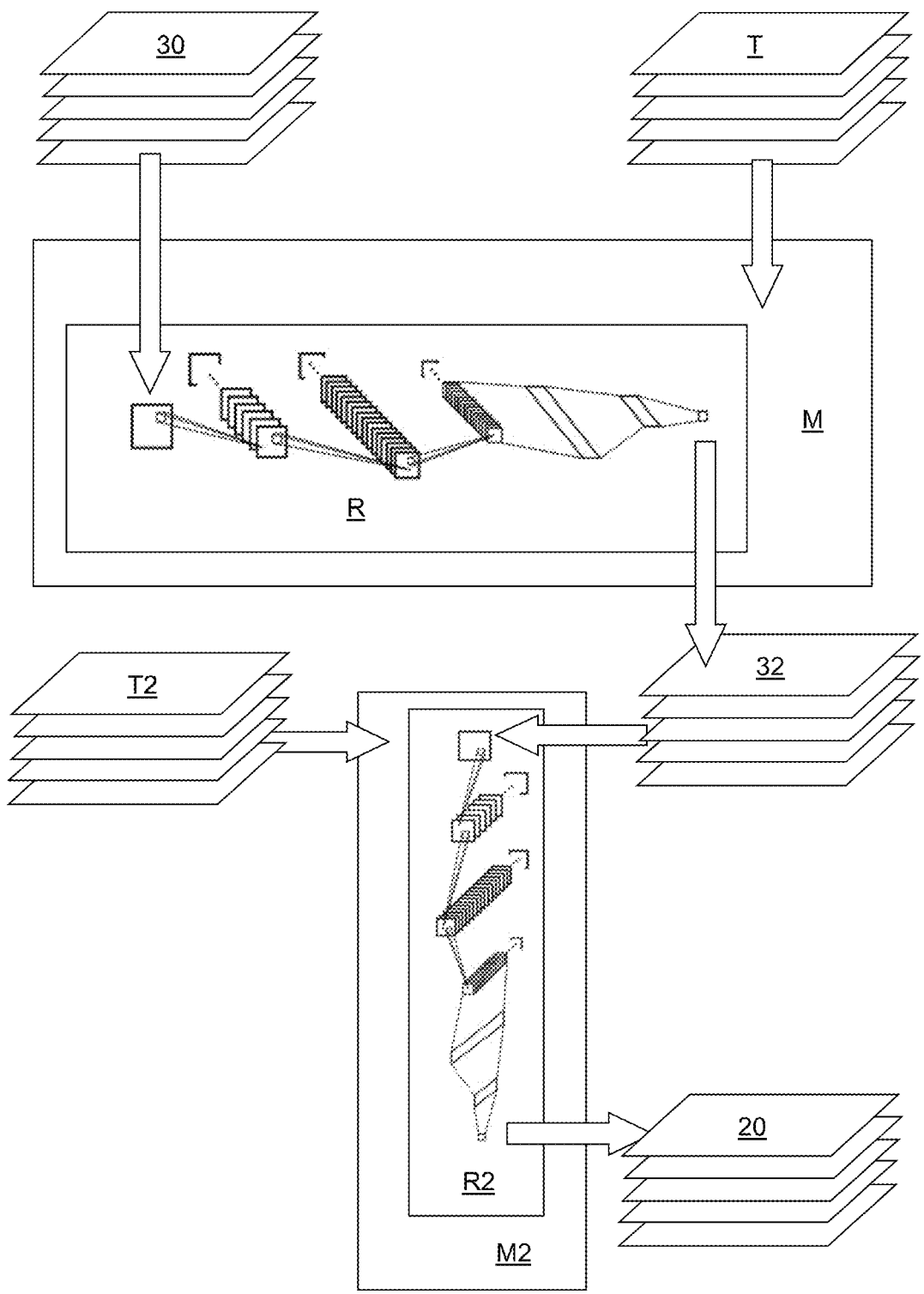
FIG. 8 illustrates schematically process steps of machine learning algorithms of example embodiments of the method of the invention.

FIGS. 7 and 8

The step S4 of identifying an image section with sensitive information described in relation to FIG. 6 is performed by an image processing program B. The latter comprises, in the variant embodiment of FIG. 7, a reference model R of a machine learning algorithm M. In a preceding training process, parameters of the model (model weights) are determined. These model weights constitute the reference information i.

FIG. 7 illustrates a training process for which training images 30 and associated target images T are used. For example, the target images T can correspond to the training images 30, wherein an image section with sensitive information is respectively tagged. The target images T can have been generated manually. The reference model R receives each of the training images 30 as input and calculates an output from the same. For this calculation, the reference model R uses parameters/model weights whose final values are yet to be determined at the beginning of the training. The output of the reference model R is an output image 32 here. The machine learning algorithm M uses a loss function L or alternatively a reward function, which calculates a deviation between a current output image 32 and an associated target image T. As a function of this deviation, an optimization function of the machine learning algorithm M modifies the current model weights of the reference model R. The described processes are repeated until the loss function L is minimized or an alternative reward function is maximized. The model weights determined upon completion of this training are then used when a microscope image 10 is fed to the reference model R.

In a variant of the described example embodiment, the target images T are replaced by target data consisting of image coordinates or other details that identify one or more image sections of the respectively associated training image 30. Correspondingly, the output of the reference model R likewise consists of image coordinates or other details by means of which image sections are defined.

The image sections identified by the reference model R are subsequently rendered unrecognizable. This can occur via classic image processing means or by means of a second machine learning algorithm, which is illustrated in FIG. 8. The second machine learning algorithm M2 comprises a second reference model R2, which receives the output image 32 of the (first) machine learning algorithm M as input. The image sections tagged in the output images 32 are rendered unrecognizable in associated target images T2 for the second machine learning algorithm M2, whereby the second machine learning algorithm M2 learns to calculate an anonymized image 20 in which the relevant image sections are unrecognizable from an output image 32 as input.

Alternatively, the reference model R shown in FIG. 7 can also be used to identify and render unrecognizable image sections with sensitive information simultaneously. To this end, the target images T described in the foregoing are replaced with target images in which image sections with sensitive information have been rendered unrecognizable (for example manually). By means of such training data, the machine learning algorithm M learns fitting parameters in order to calculate an anonymized image 20 as an output from a microscope image 10 as input in a single process step.

In the examples illustrated in FIGS. 7 and 8, a supervised learning process using a deep learning model is implemented, for example using an image-to-image CNN (convolutional neural network) or a GAN (generative adversarial network). In some embodiments, it is also possible to implement an unsupervised or partially supervised learning process.

Figure 9:
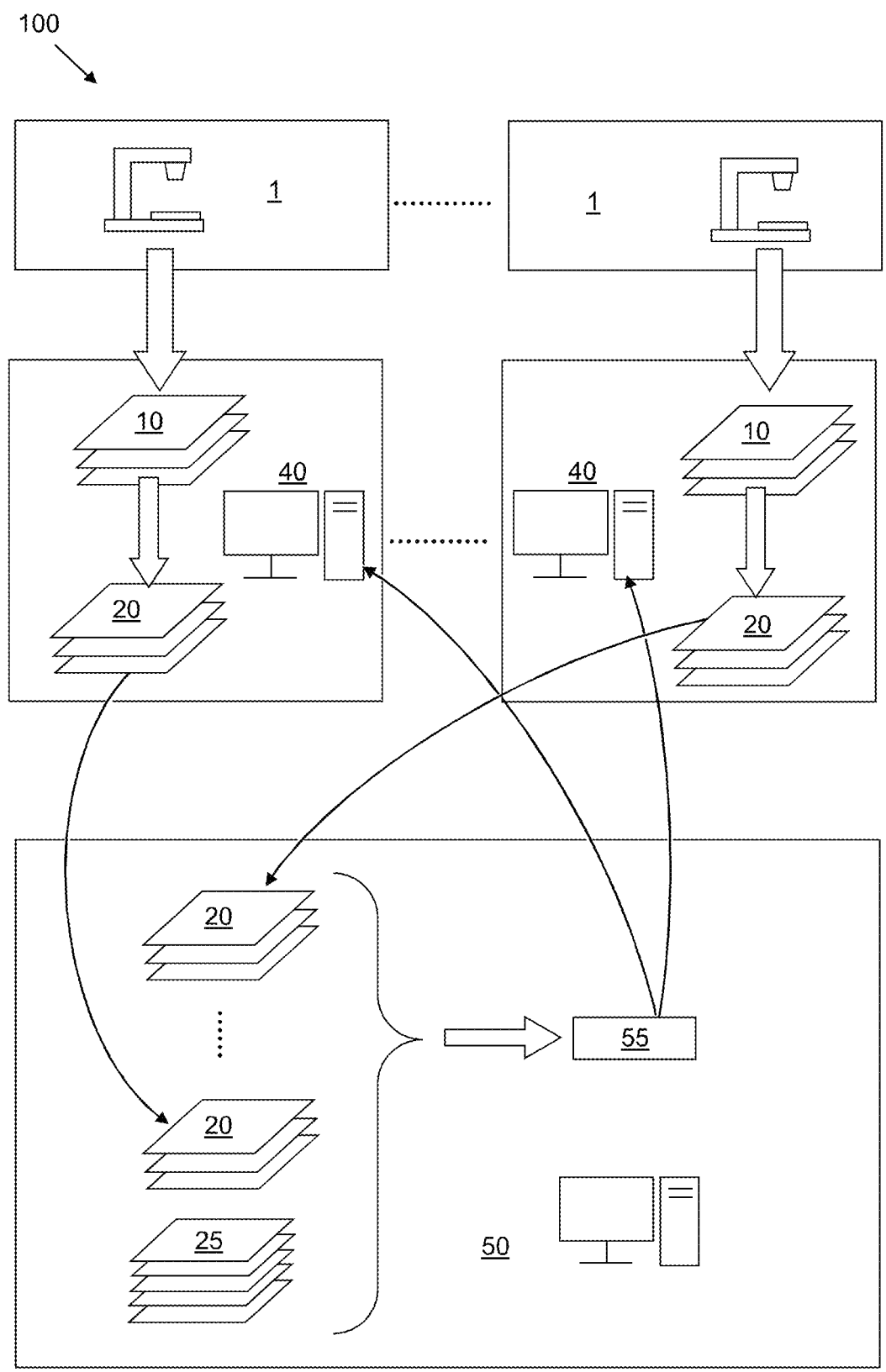
FIG. 9 shows schematically an example embodiment of a microscopy system of the invention.

Example Embodiment of FIG. 9

FIG. 9 shows an example embodiment of a microscopy system 100 according to the invention and illustrates an example embodiment of a method according to the invention for utilizing microscope images 10. A plurality of microscopes 1 respectively capture one or more microscope images 10 which they then transmit to a respective computing device 40. The computing devices 40 generate anonymized images 20 from the microscope images 10 in the manner described in the foregoing. The computing devices 40 subsequently transmit the anonymized images 20 to a central computing device 50. The central computing device 50 is configured to exploit the anonymized images 20 of a plurality of computing devices 40 and thus of a plurality of microscopes 1 for a joint data analysis. For example, the anonymized images 20, which originate at different microscopes 1, can be used collectively as training data for a machine learning application 55. The training data can optionally comprise further images 25. Using this training data, the central computing device determines model parameters of, for example, an image processing application, which is then transmitted to the different computing devices 40. The computing devices 40 can now evaluate microscope images 10 using the imaging processing application. All computing devices 40 thus profit from the training data extracted from information contained in the microscope images of different computing devices without it being necessary for the computing devices to share microscope images with sensitive information.

The different described variants of the invention enable an exploitation of relevant information of microscope images for numerous applications in which a sharing or use of data would otherwise not be possible or at the very least would be undesirable due to the sensitive information in the microscope images. A manual removal of information from a microscope image or from the sample carrier by a microscope user is unnecessary. The described example embodiments are purely illustrative and variants of the same are possible within the scope of the attached claims.

LIST OF REFERENCES

1 Microscope
2 Objective
3 Optical axis of the objective 2
4 Condenser
5 Microscope stand
6 Microscope camera
7 Overview camera
8 Field of view of the overview camera
9 Sample stage
10 Microscope image
11 Image section in the microscope image
12 Sample carrier
13 Slide cover area
14 Descriptive field
15 Sample
16 Specific sample structures
20 Anonymized image
21 Area rendered unrecognizable
25 Images
30 Training images
32 Output images
40 Computing device
50 Central computing device
55 Machine learning application
100 Microscopy system
B Image processing program
i Reference information regarding sensitive information
i1-i4 Selection of options concerning the type of sensitive information
M Machine learning algorithm
M2 Second machine learning algorithm
R Reference model
R2 Second reference model
S1-S7 Method steps
T, T2 Target images

We claim:

1. A method for processing microscope images, comprising:
acquiring a microscope image captured by a microscope;
identifying at least one image section with sensitive information within the microscope image using an image processing program which uses provided reference information regarding sensitive information;
rendering unrecognizable the at least one identified image section with sensitive information in order to generate an anonymized image; and
outputting the anonymized image,
wherein the image processing program performs a classification of the microscope image by which the microscope image is assigned to an image class,
wherein a position of an image section with sensitive information is respectively stored as reference information for different image classes, and
wherein the identification of at least one image section with sensitive information occurs by using the position stored for the determined image class.

2. The method as defined in claim 1,
wherein the microscope image is an overview image of a sample carrier or a sample image of a microscopic sample.

3. The method as defined in claim 1,
wherein the reference information regarding sensitive information relates to one or more of the following: text, adhesive labels or markings on sample carriers, a slide cover area of a sample carrier; one or more sample chamber areas; one or more sample areas on a sample carrier; or a background area outside the sample carrier;
wherein the microscope image is an overview image and wherein the at least one image section with sensitive information comprises text, an adhesive label, a marking on the sample carrier, a slide cover area, one or more sample chamber areas, one or more sample areas on a sample carrier, or a background area outside a sample carrier.

4. The method as defined in claim 1,
wherein the predetermined reference information regarding sensitive information relates to one or more sample types, wherein the sample types are one or more of: biological cells, cell organelles, tissue sections, pathology data or manufacturer/product designations.

5. The method as defined in claim 1,
wherein a user is presented with a selection of options concerning the type of sensitive information for which corresponding image sections are to be rendered unrecognizable,
wherein the provided reference information relates to different types of sensitive information,
wherein the identification and rendering unrecognizable of image sections only includes image sections that relate to the types of sensitive information selected by the user.

6. The method as defined in claim 1,
wherein the image processing program selects the types of sensitive information for which corresponding image sections are rendered unrecognizable, based on an image content of the microscope image or a contextual datum relating to the microscope image.

7. The method as defined in claim 6,
wherein the image processing program performs the selection of the types of sensitive information depending on one or more of the following factors:
as a function of whether the microscope image is an overview image or a sample image;
as a function of parameters and settings on a microscope stand or of a microscope component;
as a function of a file name of the microscope image or a detail linked to a file of the microscope image;
as a function of a sample type or a sample carrier type used when the microscope image was captured;
as a function of a text content on a sample carrier.

8. The method as defined in claim 1,
wherein a shape is predetermined for the at least one image section, whereby the shape of the at least one image section is disassociated from a shape associated with the sensitive information.

9. The method as defined in claim 1,
wherein the image processing program comprises a trained reference model of a machine learning algorithm, which performs the identification of the at least one image section with sensitive information, wherein the reference information regarding sensitive information is provided in the form of model parameters in the trained reference model.

10. The method as defined in claim 9, further comprising:
training the reference model of the machine learning algorithm in order to define the model parameters, wherein the training occurs with pairs each including a training image and an associated target image, wherein training images contain image sections with sensitive information and wherein areas corresponding to these image sections in terms of their position are tagged or rendered unrecognizable in the associated target images.

11. The method as defined in claim 9,
wherein the reference model of the machine learning algorithm also performs the operation of rendering the at least one image section unrecognizable.

12. The method as defined in claim 1,
wherein the image processing program identifies the at least one image section with sensitive information using segmentation or detection.

13. The method as defined in claim 1,
wherein the image processing program comprises at least one of:
a neural network trained using a machine learning algorithm, which generates the anonymized image directly from the microscope image, to which end the neural network is trained with pairs each including a training image and an associated target image, wherein training images contain image sections with sensitive information and areas corresponding to these image sections in terms of their position are rendered unrecognizable in the associated target images; and an autoencoder which is trained with a machine learning algorithm using training images that do not contain any image sections with sensitive information in order to generate the anonymized image directly from the microscope image.

14. The method as defined in claim 1,
wherein the operation of rendering an identified image section unrecognizable occurs by
pixelating, adding noise to or blurring the identified image section; or
replacing the identified image section or parts of the same using image content from a surrounding area; or
excising or truncating the identified image section; or
replacing the identified image section with a predetermined content, a predetermined pattern or a predetermined colour; or
deleting content of a certain colour channel of the microscope image at least in the identified image section.

15. The method as defined in claim 1,
wherein the operation of rendering an identified image section unrecognizable occurs by feeding the identified image section to:
a neural network trained to fill an image region based on contextual data from adjacent regions and by replacing the identified image section with an output of the neural network; or
an autoencoder, which generates an output therefrom that replaces the identified image section, wherein the autoencoder is trained with training images that do not contain any sensitive information.

16. The method as defined in claim 1,
wherein a type of operation for rendering an image section unrecognizable occurs as a function of the sensitive information, wherein, when the sensitive information contained in the image section is text, the operation of rendering the identified image section unrecognizable occurs by replacement with image content from a surrounding area, while, when the sensitive information contained in the image section is not text, the operation of rendering the identified image section unrecognizable occurs in a manner other than by replacement with image content from a surrounding area.

17. A computer program with commands which are stored on a non-transitory computer-readable medium and which, when the computer program is executed by computer, cause the execution of the method defined in claim 1.

18. A method for utilizing microscope images,
wherein a plurality of computing devices respectively execute a method for processing microscope images, the method including:
acquiring a microscope image;
identifying at least one image section with sensitive information within the microscope image with an image processing program which uses provided reference information regarding sensitive information;
rendering unrecognizable the at least one identified image section with sensitive information in order to generate an anonymized image; and
outputting the anonymized image;
such that each of the plurality of computing devices outputs at least one anonymized image;
wherein the plurality of computing devices transmit the anonymized images to a central computing device that does not have access to the captured microscope images; and
wherein the central computing device performs a joint data evaluation of the anonymized images.

19. The method as defined in claim 18, wherein at least one of the plurality of computing devices displays the anonymized image to a user for release approval and transmits the anonymized image to the central computing device only after release approval has been given.

20. The method as defined in claim 18,
wherein the central computing device uses the anonymized images for training images of a machine learning application and transmits the trained machine learning application to the computing devices upon completion of the training.

21. A microscopy system, comprising:
at least one microscope for capturing a microscope image; and
at least one computing device configured to:
identify at least one image section with sensitive information within the microscope image with an image processing program which uses provided reference information regarding sensitive information;
render unrecognizable the at least one identified image section with sensitive information in order to generate an anonymized image; and
output the anonymized image;
wherein the reference information regarding sensitive information relates to one or more of the following: text, adhesive labels or markings on sample carriers, a slide cover area of a sample carrier; one or more sample chamber areas; one or more sample areas on a sample carrier; or a background area outside the sample carrier; and
wherein the at least one image section with sensitive information comprises text, an adhesive label, a marking on the sample carrier, a slide cover area, one or more sample chamber areas, one or more sample areas on a sample carrier, or a background area outside a sample carrier.

22. A method for processing microscope images, the method comprising:
acquiring a microscope image captured by a microscope;
identifying at least one image section with sensitive information within the microscope image with an image processing program which uses provided reference information regarding sensitive information;
rendering unrecognizable the at least one identified image section with sensitive information in order to generate an anonymized image; and
outputting the anonymized image;
wherein the image processing program comprises a trained reference model of a machine learning algorithm, which performs the identification of the at least one image section with sensitive information, wherein the reference information regarding sensitive information is provided in the form of model parameters in the trained reference model.

23. A method for processing microscope images, the method comprising:
acquiring a microscope image captured by a microscope;
identifying at least one image section with sensitive information within the microscope image with an image processing program which uses provided reference information regarding sensitive information;
rendering unrecognizable the at least one identified image section with sensitive information in order to generate an anonymized image; and
outputting the anonymized image;
wherein the image processing program comprises at least one of:
a neural network trained with a machine learning algorithm, which generates the anonymized image from the microscope image, to which end the neural network is trained with pairs each including a training image and an associated target image, wherein training images contain image sections with sensitive information and areas corresponding to these image sections in terms of their position are rendered unrecognizable in the associated target images;
an autoencoder which is trained with a machine learning algorithm using training images that do not contain any image sections with sensitive information in order to generate the anonymized image directly from the microscope image;
a neural network trained to fill an image region based on contextual data from adjacent regions and by replacing the identified image section with an output of the neural network for rendering the identified image section unrecognizable; or
an autoencoder, which generates an output from at least the identified image section that replaces the identified image section for rendering the identified image section unrecognizable, wherein the autoencoder is trained with training images that do not contain any sensitive information.

* * * * *